United States Patent
Collins et al.

(10) Patent No.: US 7,108,790 B2
(45) Date of Patent: Sep. 19, 2006

(54) METHOD AND APPARATUS FOR GENERATING A STERILE INFUSION FLUID

(75) Inventors: Gregory R. Collins, Monroe, NY (US); James Summerton, Hillsdale, NJ (US); Edward Spence, Bronx, NY (US)

(73) Assignee: Nephros, Inc., New York, NY (US)

( * ) Notice: Subject to any disclaimer, the term of this patent is extended or adjusted under 35 U.S.C. 154(b) by 378 days.

(21) Appl. No.: 10/399,676

(22) PCT Filed: Oct. 19, 2001

(86) PCT No.: PCT/US01/50719

§ 371 (c)(1),
(2), (4) Date: Oct. 8, 2003

(87) PCT Pub. No.: WO02/32476

PCT Pub. Date: Apr. 25, 2002

(65) Prior Publication Data

US 2004/0045881 A1    Mar. 11, 2004

Related U.S. Application Data

(60) Provisional application No. 60/241,662, filed on Oct. 19, 2000.

(51) Int. Cl.
  *B01D 61/26* (2006.01)
  *B01D 61/32* (2006.01)
  *B01D 65/00* (2006.01)

(52) U.S. Cl. .................. 210/650; 210/85; 210/86; 210/87; 210/97; 210/136; 210/137; 210/143; 210/252; 210/257.1; 210/258; 210/321.71; 210/323.1; 210/739; 210/741; 210/805

(58) Field of Classification Search .............. 210/85, 210/86, 87, 90, 97, 103, 104, 109, 117, 121, 210/136, 137, 143, 195.2, 252, 258, 257.1, 210/257.2, 645, 646, 739, 741, 744, 805, 210/101, 323.1, 321.65, 321.71, 650
See application file for complete search history.

(56) References Cited

U.S. PATENT DOCUMENTS

| | | | |
|---|---|---|---|
| 4,107,039 A | 8/1978 | Lindsay, Jr. et al. | |
| 4,388,184 A | 6/1983 | Brous et al. | |
| 4,702,829 A | 10/1987 | Polaschegg et al. | |
| 4,708,802 A | 11/1987 | Rath et al. | |
| 4,834,888 A | 5/1989 | Polaschegg | |
| 5,567,320 A | 10/1996 | Goux et al. | |
| 5,660,722 A | 8/1997 | Nederlof | |
| 5,744,027 A | 4/1998 | Connell et al. | |
| 5,808,181 A | 9/1998 | Wamsiedler et al. | |
| 5,932,103 A | 8/1999 | Kenley et al. | |
| 6,139,748 A * | 10/2000 | Ericson et al. ............... | 210/646 |

\* cited by examiner

FOREIGN PATENT DOCUMENTS

EP    0 904 789 A2    3/1999

*Primary Examiner*—John S. Kim
(74) *Attorney, Agent, or Firm*—Darby & Darby

(57) ABSTRACT

An apparatus and method are provided for generating sterile infusion fluid from non-sterile infusion fluid produced by a machine. In one embodiment, the sterile infusion fluid is produced by a sterile fluid generating device that is an ancillary device designed to operate in conjunction with the existing machine. For example, the sterile fluid generating device is used in conjunction with a dialysis machine according to one embodiment resulting in sterile infusion fluid being produced.

27 Claims, 12 Drawing Sheets

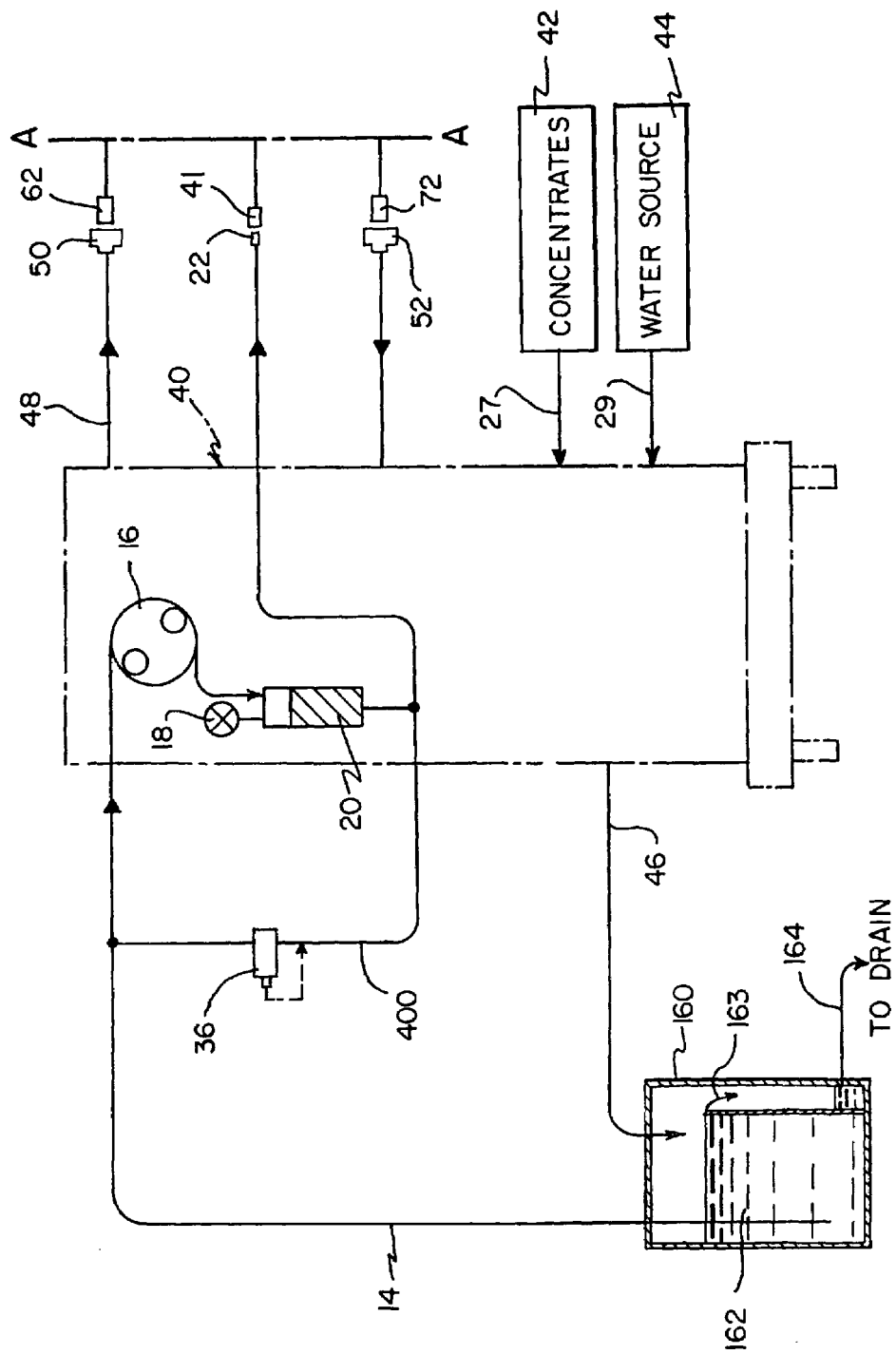

METHOD AND APPARATUS FOR GENERATING A STERILE INFUSION FLUID

CROSS-REFERENCE TO RELATED APPLICATION

This is a U.S. national phase application under 35 U.S.C. §371 of International Patent Application No. PCT/US01/50719 filed Oct. 19, 2001 and claims the benefit of U.S. patent application Ser. No. 60/241,662, filed Oct. 19, 2000, which is hereby incorporated by reference in its entirety. The International Application was published in English on Apr. 25, 2002 as WO 02/32476 A2 under PCT Article 21(2).

FIELD OF THE INVENTION

The present application relates to the production and supply of sterile fluids in general and, more particularly, to a device for generating sterile infusion fluid "on site" for blood-cleansing applications, such as hemodialysis, hemofiltration, hemodialfiltration, or peritoneal dialysis, to name a few.

BACKGROUND OF THE INVENTION

Sterile infusion fluid is used in various medical applications, particularly in blood-cleansing applications such as hemodialysis, hemofiltration, hemodiafiltration, or peritoneal dialysis treatments. In hemodialysis, for example, the infusion fluid is generally used to prime an extracorporeal circuit of a blood-cleansing machine, prior to connecting a patient to the machine, and to rinse back the patient's blood at the end of the treatment. Sterile fluid may also be administered to patients in the form of a bolus, which may improve the patient's fluid status, blood pressure, etc. In tile practice of hemodiafiltration, plasma water is removed by filtration from the blood as it traverses through the hemodialyzer cartridge and certain toxins or other material diffuses from the patient's blood. To compensate for this loss of plasma water, sterile fluid must be added either upstream or downstream of the hemodialyzer cartridge. The sterile fluid used in these applications is generally a normal saline solution (e.g., a solution having a sodium chloride concentration of 0.9 percent by weight) which is supplied pre-sterilized in one or two liter flexible bags. In some cases a Ringer's Lactate Solution might be used. In peritoneal dialysis, sterile dialysate packaged in flexible bags is typically infused into and subsequently emptied from the patient's peritoneal cavity.

In dialysis clinics that have multiple dialysis stations, the clinic must purchase and store large volumes of sterile fluid. The costs involved in buying and storing the pre-packaged sterile fluid may be significant. Further, peritoneal dialysis patients are typically treated at home and thus, the cost and storage capacity for the required amounts of sterile fluid, as much as 12 liters per day, become even more significant.

SUMMARY OF THE INVENTION

In one aspect, it is an object to generate a sterile fluid "on-site", thereby to reduce or eliminate the costs associated with purchasing and storing large volumes of sterile fluid.

There are a variety of machines that are designed to produce non-sterile fluids. For example, one such machine is a dialysis machine that, in normal operation, proportions dialysate concentrates and water to generate a dialysate fluid (a non-sterile fluid). The dialysate fluid contains various electrolytes (e.g., sodium ions, chloride ions, potassium ions, magnesium ions, etc.) at concentrations compatible with the patient's blood. Although in the practice of hemodialysis, the dialysate fluid must meet certain quality requirements it is not necessary that the dialysate fluid be sterile. The non-sterile fluid is acceptable because, during the dialysis process the patient's blood is protected by a dialyzer membrane which acts as a sterile barrier between the dialysate fluid and the blood.

The present application is directed to a method and a device for generating a sterile infusion fluid. The method and device can be implemented in a number of ways, depending on particular needs. In accordance with one embodiment, the sterile fluid generating device is an ancillary device designed to operate in conjunction with an existing dialysis machine, e.g., when the machine is not performing hemodialysis treatments or used in other treatment or cleaning operations. In this embodiment, the dialysis machine serves as a source of non-sterile dialysate fluid. This dialysate fluid is supplied to the ancillary device which filters the dialysate fluid in accordance with a method recited herein, whereby dialysate fluid is filtered in a safe manner to render a sterile and non-pyrogenic fluid which meets predetermined requirements to make it of injectable quality. The sterile fluid produced by the present invention may be designed to replace any type of sterile fluid used in medical processes, e.g. as a normal saline solution, peritoneal dialysate fluid, Ringer's lactate solution, etc., depending on the application.

It will be appreciated by persons skilled in the art that the present invention is not limited to the particular sterile fluid applications described herein, namely, hemodialysis, hemofiltration, hemodialfiltration, and peritoneal dialysis. The sterile fluid generated by the methods and devices of the various embodiments disclosed herein can be suitable for use in any other application that may benefit From the advantages described herein.

BRIEF DESCRIPTION OF THE DRAWINGS

FIGS. 6A and 6B, when joined at the match line A—A, are a schematic illustration of a fluid sterilization system in accordance with a sixth embodiment similar to the embodiment of FIGS. 3A and 3B.

DETAILED DESCRIPTION OF THE INVENTION

Figure 1A:
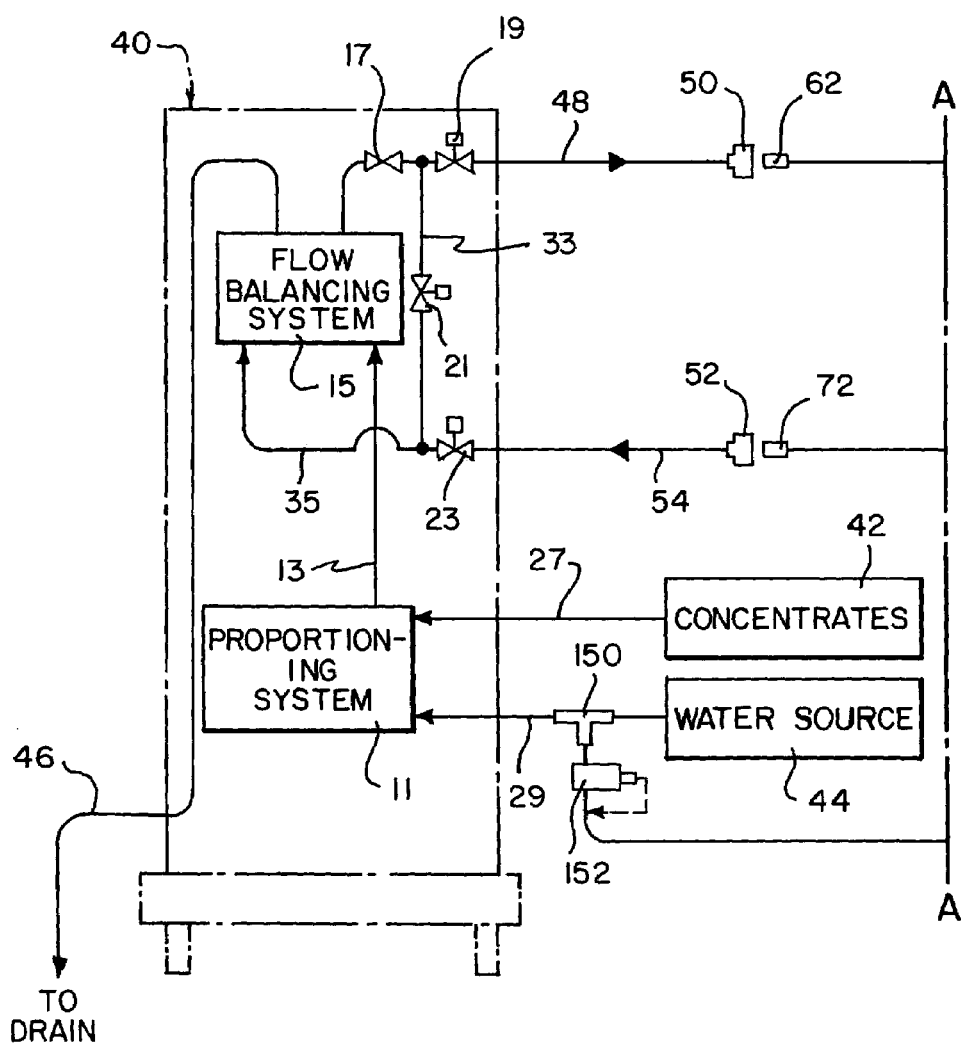
FIGS. 1A and 1B, when joined at match line A—A, are a schematic illustration of a fluid sterilization system in accordance with a first embodiment, used in conjunction with a machine that produces a non-sterile fluid that is then filtered using the fluid sterilization system.
Figure 1B:
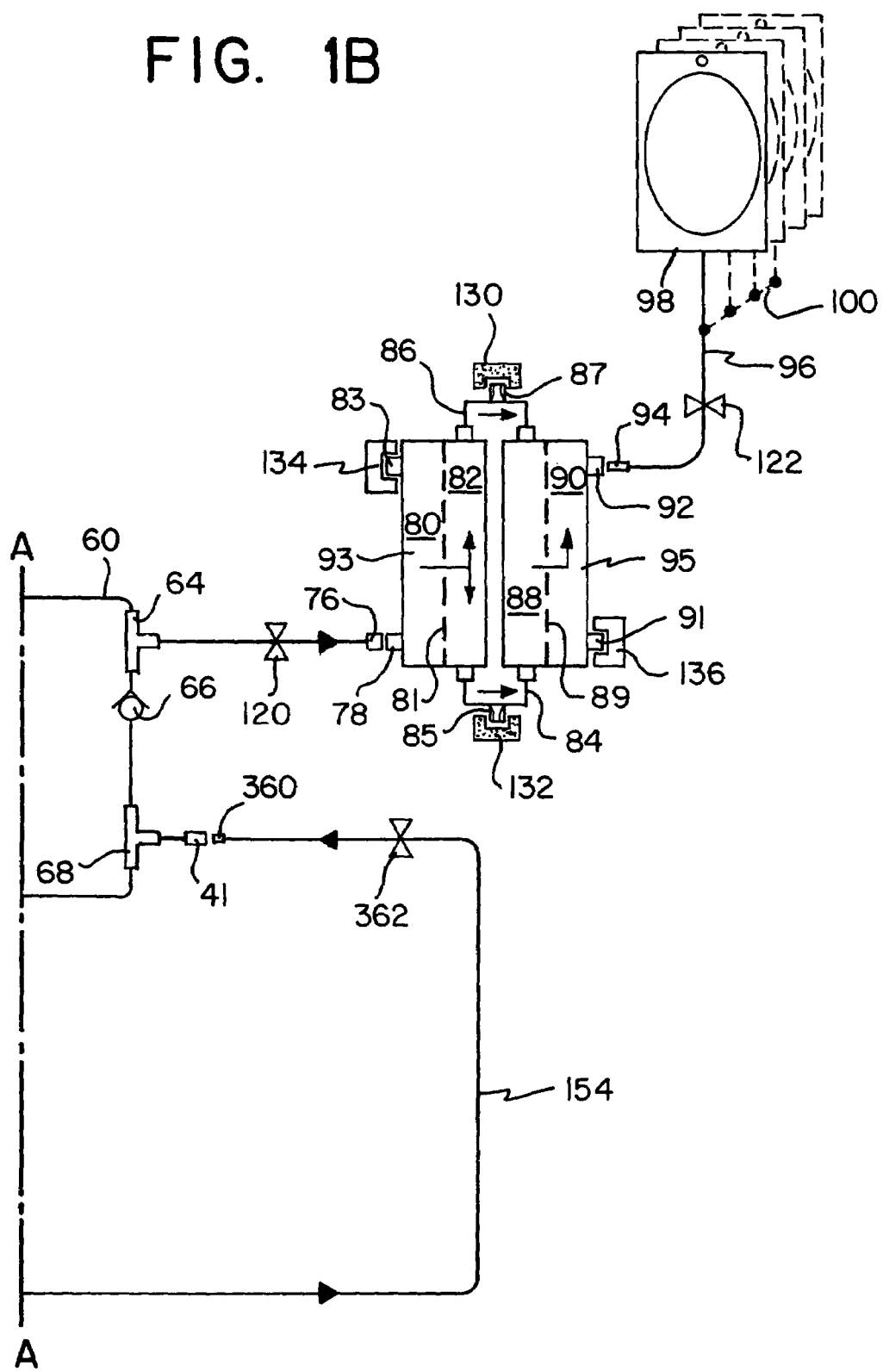

Reference is made to FIGS. 1A and 1B which illustrate a first embodiment. In this embodiment, a machine 40 is used as source of non-sterile fluid. The machine 40 can be of any number of types of machines that produce non-sterile fluid. For example, one such machine 40 is a dialysis machine that produces non-sterile dialysate fluid. Suitable dialysis machines 40 may include but are not limited to the Fresenius 2008E or 2008H, available from Fresenius of Lexington, Mass., the Althin System 1000, available from Baxter/Althin of Miami Lakes, Fla., the Cobe Centrysystem 3, available from Gambro/Cobe of Lakewood, Colo. Dialysis machine 40 includes a proportioning system 11 that mixes water 44 and dialysate concentrates 42 at a suitable proportion to produce a dialysate solution 13 of a predetermined concentration. Dialysis machine 40 preferably includes a fail-safe mechanism which ensures that the final concentration of the dialysate solution delivered to a dialyzer is within physiologic limits (i.e. compatible with the ionic concentration of blood). This may be accomplished by placing a conductivity sensing device 17 in the dialysate stream 31 followed by a series of valves 19, 21, and 23 and a bypass conduit 33. In the event that the conductivity as measured by the conductivity sensing device 17 is outside predetermined limits, valves 19 and 23 are closed while valve 21 is opened to redirect the improperly proportioned dialysate fluid through the bypass conduit 33.

Additionally, dialysis machine 40 preferably includes a fluid balance system 15 (flow balancing system), which controls the flow rates or volumes of the dialysate fluid leaving the dialysis machine 40 though conduit 48 and the dialysate fluid returning to the dialysis machine 40 via a dialysate return conduit 54. According to this first embodiment, a dialysate supply connector 50 and a dialysate return connector 52 of the dialysis machine 40 are connected to a dialysate inlet connector 62 and dialysate outlet connector 72 associated with the sterilization system.

Between connectors 62 and 72 is a fluid conduit 60, that includes a first branch or tee connector 64, a one way check valve 66 or similar type valve, and a second branch or tee connector 68. The first branch connector 64 is used to conduct a portion of the fresh non-sterile dialysate fluid to a filtration assembling including sterilizing filters 93 and 95, while the second branch connector 68 is used to conduct a similar amount of fluid into the fluid conduit 60 from an external source so as to satisfy the dialysis machine fluid balance system. According to this embodiment, the sterilizing filters 93 and 95 preferably contain semi-permeable membranes 81 and 89, respectively. Each of the membranes 81, 89 preferably has a relatively high water permeability property and a molecular weight cut-off small enough to retain bacteria, endotoxin, and other potential particulate that may be present in the non-sterile dialysate fluid. A desirable range for molecular weight cut-off for the sterilizing filters is about 5K–35K Daltons; however, this will depend upon the precise application. The sterilizing filters 93, 95 may be medium or high flux dialyzers, hemofilters, or other commercially available fluid sterilizing filters, such as used to sterilize pharmaceutical solutions and the like by conventional filtration methods. Examples of dialyzers and hemofilters that can be used as sterilizating filters include Fresenius dialyzers F40, F50, F60, F70, F80, F60M. F80M, available from Fresenius of Lexington, Mass., Baxter dialyzers CT 110G, CT190G, Syntra 160, available from Baxter of Deerfield, Ill., Althin Altraflux dialyzers 140, 170, 200, available from Baxter/Althin, Miami Lakes, Fla., Hospal dialyzers Filtral 12, 16, 20, available from Hospal of Meyzieu, France, and Minntech hemofilters Hemocor HPH 400, 1000, 1400, available from Minntech Corporation, Minneapolis, Minn. Other available filters that may be used as sterilizing filters include Amicon hollow fiber membrane cartridges H15P10-43, H15P30-43, available from Millipore, Bedford, Mass.

A method of generating a sterile fluid in accordance with the embodiment of FIGS. 1A and 1B is described below. Fresh water 44, meeting the water quality requirements described per the AAMI Standards for Hemodialysis Systems RD5-1992, is supplied to the dialysis machine 40. Precautions concerning machine disinfection and rinsing should be done in accordance with dialysis machine operation instructions. Once the machine 40 has been adequately rinsed, dialysate concentrates 42 are supplied to the dialysis machine 40 with the machine 40 set to produce a desired flow rate of dialysate fluid. The machine 40 is then placed in a mode that begins to draw in the concentrates 42 and the fresh water 44 at predetermined proportions per the proportioning system 11, resulting in a dialysate fluid 13 that is compatible with human blood but may not be sterile and may not be non-pyrogenic at this point. This mode may be a set-up mode or a priming mode which generally precedes a machine treatment mode. The proportioned dialysate fluid 13 is delivered to the flow balancing system 15 of the dialysis machine 40. The flow balancing system 15 can include volumetric balance chambers or dual flow meters as are known in the art.

To ensure the dialysate fluid 13 is proportioned correctly by the proportioning system 11, the conductivity of the dialysate fluid exiting flow balancing system 15 is generally measured by a conductivity sensing device 17. This in combination with a series of valves 19, 21, and 23, form a fail-safe mechanism that prevents improperly proportioned dialysate fluid from exiting the dialysis machine 40 via the conduit 48 when the dialysate supply and return connectors 50 and 52 are not connected to their respective dialysis machine rinse ports (not shown). For example, when the dialysate conductivity is outside predetermined limits, valves 19 and 23 are closed while 21 is opened. This shunts the improperly proportioned dialysate fluid though the bypass conduit 33 and back to the flow balancing system 15. The improperly proportioned dialysate fluid then flows through a conduit 46 leading out to a drain.

When the conductivity is within the predetermined limits, the bypass valve 21 is closed and valves 19 and 23 are opened. This allows properly proportioned dialysate fluid to flow through the dialysate supply conduit 48, through conduit 60, and into the dialysate return conduit 54 which leads back to the flow balancing system 15 and then to a drain or the like. In order to get a portion of the dialysate fluid to pass through the sterilizing filters 93, 95 via conduit 74, fluid under pressure is injected into conduit 60 at the branched tee connector 68. This can be accomplished by opening a clamp 362 of a conduit 154 that is in fluid communication with a fresh water source 44 that typically operates above 15 to 20 psi. A pressure regulator 152 is used to regulate the downstream fluid pressure inside the conduit 154 to a desired level. This setting, which is set to between 2 to 10 psi, preferably between 3 to 6 psi, provides a means to control how fast this fluid is injected into the dialysate path. The precise setting will depend upon a number of factors, including factors that are application specific, such as the type of sterilizing filters 93, 95, etc. For example, the fluid pressure can be increased to an elevated pressure beyond 10 psi (e.g., 15 psi) so long as the diaslysis machine 40 is capable of operating at this elevated pressure and so long as the sterilization filters 93, 95 can withstand such an elevated pressure. It will therefore be appreciated that the user will set and adjust the setting so that the proper and desired amount of non-sterile dialysate fluid is flowing into the filtration assembly (sterilizing filters 93, 95), while at the same time this elevated pressure is within operating conditions for the machine 40 and the sterilizing filters 93, 95.

The flow balancing system 15 serves to regulate both the dialysate supply flow rate passing through conduit 48 and the dialysate return flow rate passing through conduit 54. Generally, the flow balance system 15 regulates the flow rates so that they are substantially equal or within a predetermined acceptable range. As a result of this, the injection of fresh water into the conduit 60 at the branched tee connector 68 serves to increase the fluid pressure residing in the fluid path defined by conduits 31, 48, 60, 54, and 35. This is due to the fluid conduits being relatively noncompliant. The increase in fluid pressure in conduit 60 causes a portion of the dialysate fluid to be diverted into conduit 74 that connects to the inlet port 81 of a first sterilizing filter 93.

Preferably, a second sterilizing filter 95 is used as a redundant filtration stage to assure sterility of the filtered fluid in the event one of the filter fails during the filtration process. The sterilizing filters 93, 95 can consist of two single filter cartridges, or it can consist of a single cartridge unit having multiple filtration sections. Although it is possible to use a single filtration stage (i.e. without redundant filtration) as the final filtration unit, it is generally undesirable due to patient safety issues that may arise should the filter fail during operation. Redundant filtration is generally required by industry standards.

In the embodiment of FIGS. 1A and 1B, two separate sterilizing filters 93, 95 are used. The first sterilizing filter 93 contains two compartments 80 and 82 that are separated by a semi-permeable membrane 81. Fluid to be filtered enters the inlet port 78 leading to a first upstream compartment 80. Fluid is then filtered across the semi-permeable membrane 81 and into a first downstream compartment 82. As previously mentioned, the semi-permeable membrane 81 serves to filter the non-sterile dialystate fluid and remove any impurities that may exist. The degree of filtration depends upon a number of factors, including the specific type of filter being used.

The once filtered dialysate fluid then exits the first downstream compartment 82 through outlet ports and passes through conduits 84 and 86 that leads to a second upstream compartment 88 of the second sterilizing filter 95. The once filtered dialysate fluid is then filtered across the second semi-permeable membrane 89 and flows into the second downstream compartment 90 of the second sterilizing filter 95, thereby being filtered twice. The twice filtered dialysate fluid exits the second sterilizing filter through an outlet port 92 that is in fluid communication with a sterile collection bag 98 or any other type of collection device or container that is suitable for storing a sterilized fluid. Starting and stopping the flow of dialysate fluid through the sterilizing filters 93, 95 and into the collection bag 98 may be accomplished by opening a valve, such as a tubing clamp 120 or 122. This allows a new collection bag 98 or new sterilization filters 93, 95 to be used in the process. In addition, it should be understood that number of collection bags 98 can be filled at the same time by assembling multiple bags 98 to a common manifold 100.

It should be understood that the flow rate at which the collection bag 98 is being filled should not exceed the rate at which the dialysis machine 40 is producing dialysate fluid. Preferably, the rate at which the collection bag 98 is being filled should be less than that of the dialysate flow rate such that there is a positive flow of fresh dialysate fluid though the check valve 66. This assures that the water being injected into the conduit 60 at the branched tee connector 68 will not flow in a retrograde fashion through the check valve 66. This can be further explained as follows. Provided there is a positive flow of dialysate through the check valve 66, the pressure upstream of the check valve 66, such as at the branched tee connector 74 will be higher than the pressure downstream of the check valve 66, such as at the branched tee connector 68. In this case, water that is being injected into conduit 60 at the branched connector 68 will flow toward conduit 54 leading back to the dialysis machine 40 since it cannot flow toward an area of higher pressure (i.e., towards the check valve 66 and connector 74). The rate at which sterile fluid is generated can be controlled by adjusting the pressure regulator setting 152. Increasing the output pressure, increases the filling rate while decreasing the pressure, decreases the rate. Additional factors that may affect the filling rate is the hydraulic permeability of the sterilizing filters 93, 95 and the associated hydrostatic head of the sterile collection bag 98 relative to the inlet pressure to the sterilizing filters 93, 95.

At a point when the collection bag 98 is full or when either of the clamps 120 or 122 are closed to prevent flow through the sterilizing filters 93, 95, the dialysate pressure will increase to a maximum pressure as defined by the setting of the pressure regulator 152. As known in the art, this pressure would be considered the operating pressure at the zero or no flow condition for the given pressure regulator setting. At this pressure the spring loaded diaphragm within the pressure regulator 152 closes to prevent fluid from passing through the regulator 152 (i.e. from the water source 44 into the conduit 154).

In the event that the dialysis machine 40 does not produce a properly proportioned solution, such as can occur if the concentrate solution were to run out during the process, a dialysis machine alarm condition will be generated that places the dialysis machine 40 in a safe state. In particular, the improperly proportioned dialysate will be detected by the conductivity sensing device 17 which will create an out-of-conductivity alarm condition that immediately puts the dialysate flow path into a bypass mode, i.e. valves 19 and 23 are closed and valve 21 is opened. When this occurs, flow through conduits 48 and 54 stops. Flow of water into conduit 60 at the branched tee connector 68 will then cease since flow is dead-ended in both directions. For example, closed valve 23 prevents flow toward connector 72 while check valve 66 prevents flow toward the branched tee connector 64. It will be understood by those skilled in the art, that the present apparatus and method allows only properly proportioned fluid which has been generated by the dialysis machine 40 to be filtered across the sterilizing filters 93, 95 while preventing water used to pressurize the dialysate fluid path from being filtered across the sterilizing filters 93, 95. In this respect, the invention assures that the filtered fluid collected in the sterile collection bag 98 has been properly proportioned by the dialysis machine 40 and has not been compromised or contaminated by fluid being injected into the conduit downstream of the check valve 66.

Figure 2A:
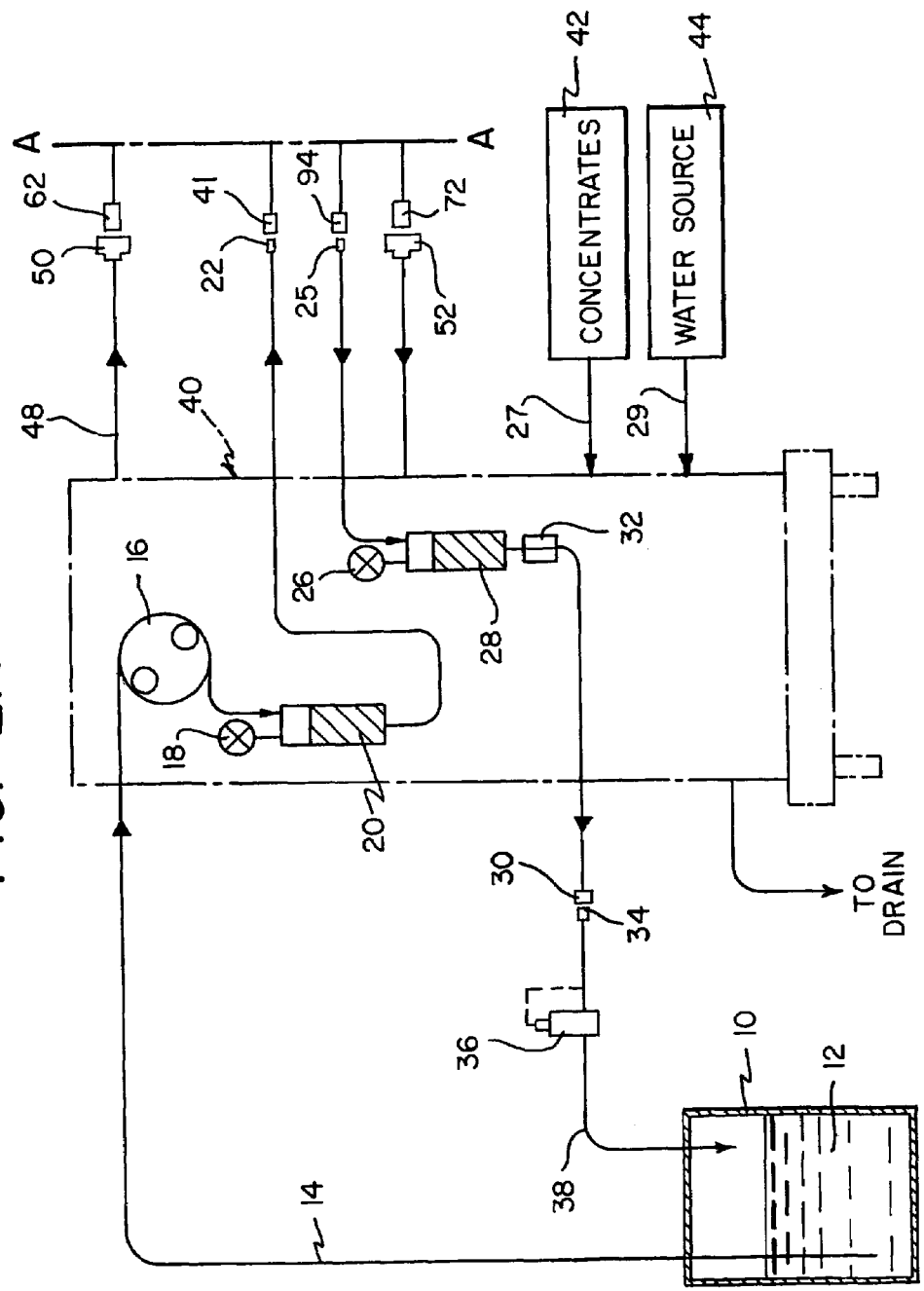
FIGS. 2A and 2B, when joined at match line A—A, are a schematic illustration of a fluid sterilization system in accordance with a second embodiment, used in conjunction with a machine that produces a non-sterile fluid that is then filtered using the fluid sterilization system.
Figure 2B:
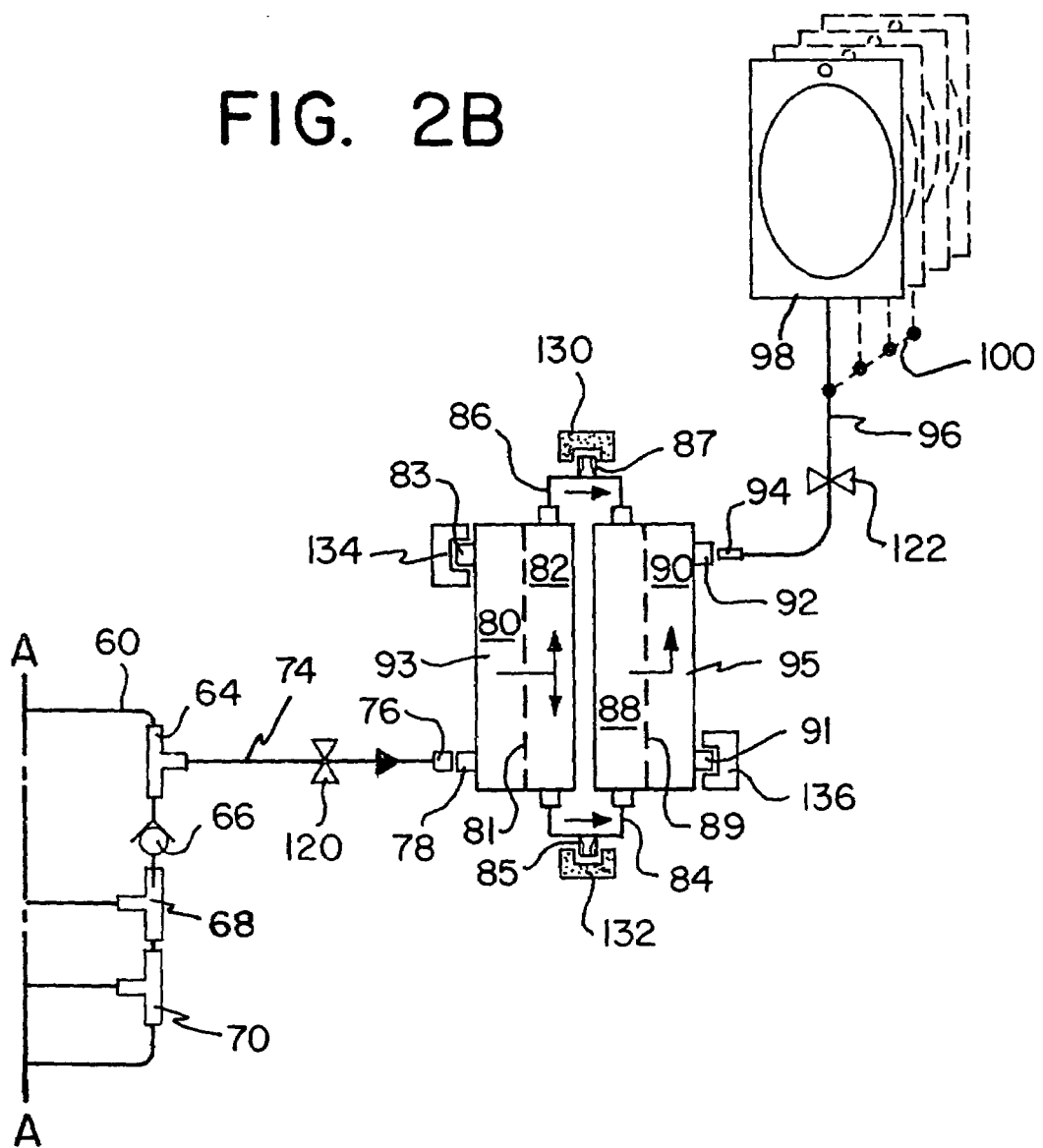

FIGS. 2A and 2B schematically illustrate an alternate configuration of the embodiment of FIGS. 1A and 1B. In the configuration of FIGS. 2A and 2B, a fluid reservoir 10 containing a fluid 12 is used instead of water from pressurized water source 44 as in FIGS. 1A and 1B. The fluid 12 contained in the reservoir 10 can be water or some other aqueous solution provided it is both miscible with the fluid being generated by the dialysis machine 40 and compatible with the materials in the dialysis machine fluid path. In order to use the fluid 12 contained in the fluid reservoir 10 in the process of making sterile fluid, it must be pressurized. This may be accomplished in several ways. In the configuration of FIGS. 2A and 2B, this is accomplished by using the dialysis machine blood pump 16, a back pressure regulating valve 36, and associated arterial and venous bloodline tubing segments 14 and 24 respectively. In this configuration, the blood pump 16 is used to draw fluid 12 from the fluid reservoir 10 and pump it through the arterial drip chamber 20 and into the dialysate path conduit 60 at the branched tee connector 68. This fluid mixes with the dialysate fluid generated by the dialysis machine 40 flowing though conduit 60 and continues toward a second branched tee connector 70 that is in fluid communication with a conduit leading back to the fluid reservoir 10. This conduit may include a venous drip chamber 28 and may pass though an air detector 32 device on the dialysis machine as is known in the art. A back pressure regulator 36 is preferably used as a means to generate a back pressure in the fluid path between the blood pump 16 and pressure regulator 36. Since a portion of this fluid path is in fluid communication with the dialysate fluid flowing through conduit 60, one is able to achieve the same effect as the pressurized water source as described in the first embodiment of FIGS. 1A and 1B. According to this embodiment, the blood pump 16 is turned on to a desired rate and air is purged from arterial and venous bloodline tubing segments. The pressure monitoring lines on the bloodline drip chambers are not connected to their respective pressure monitoring ports on the dialysis machine 40. This is to avoid creating nuisance related pressure alarms during the process of making sterile fluid. The inventors have found, however, that it may be necessary on some dialysis machines to apply a fixed pressure to the venous pressure monitoring port on the dialysis machine to avoid low TMP alarms that prevent the blood pump from operating. This may be accomplished by attaching a tubing segment to the venous pressure port, using a syringe to generate a desired venous pressure in the range of 100 to 500 mmHg, preferably 200 to 400 mmHg, followed by clamping the tubing to hold the pressure at a constant level. Since the venous pressure port on the dialysis machine is a protective mechanism to guard against a blood loss hazard when dialyzing a patient, there is no concern here since a patient is not being treated at the same time the machine is being used to make a sterile fluid. The rate at which sterile fluid is generated is primarily dependant upon the blood pump rate, the back-pressure regulator setting, the hydraulic permeability of the sterilizing filters 93, 95, and the associated hydrostatic head of the sterile collection bag 98.

One advantage of this embodiment is that it provides a means to use a separate source of fluid for those situations where the water supplied to the dialysis machine or machines may be capacity limited. Another advantage is that when the reservoir runs out of fluid, air enters the bloodline circuit and is subsequently detected by the dialysis machine air detector 32 which immediately disables the blood pump. In this manner, one can only make as much sterile fluid as initially contained in the reservoir and therefore makes it impossible to overfill the collection bag.

The embodiment of FIGS. 2A and 2B showed a method using dialysis machine blood pump and a back pressure regulating valve. It will be appreciated that a closed, pressurized fluid reservoir in fluid communication with the dialysate path can also be used, whereby pressure inside the reservoir is driven using a compressed gas source, such as air, nitrogen, etc.

Figure 3A:
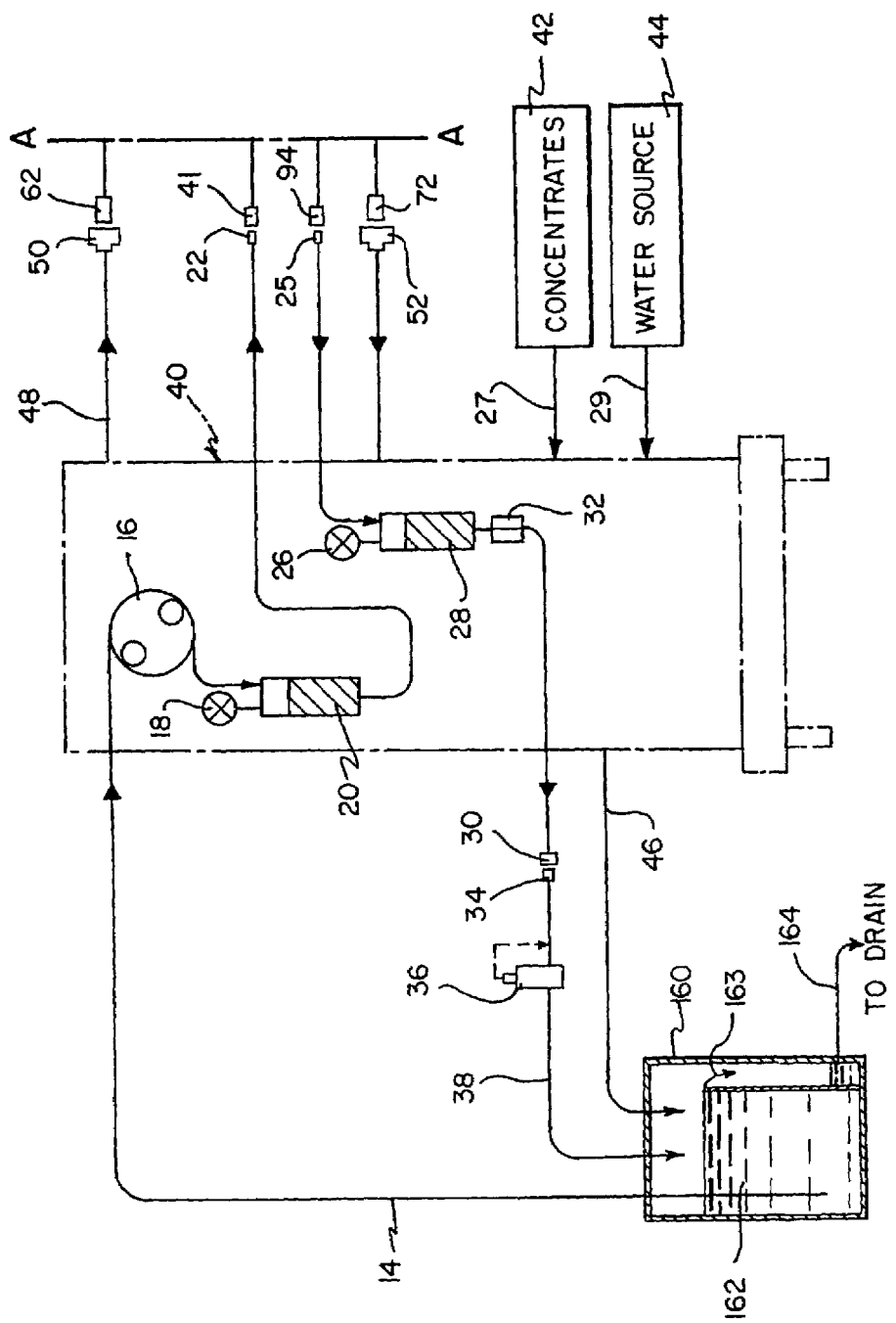
FIGS. 3A and 3B, when joined at the match line A—A, are a schematic illustration of a fluid sterilization system in accordance with a third embodiment in which the fluid sterilization system of FIGS. 2A and 2B is modified to include an overflow mechanism associated with a fluid reservoir.
Figure 3B:
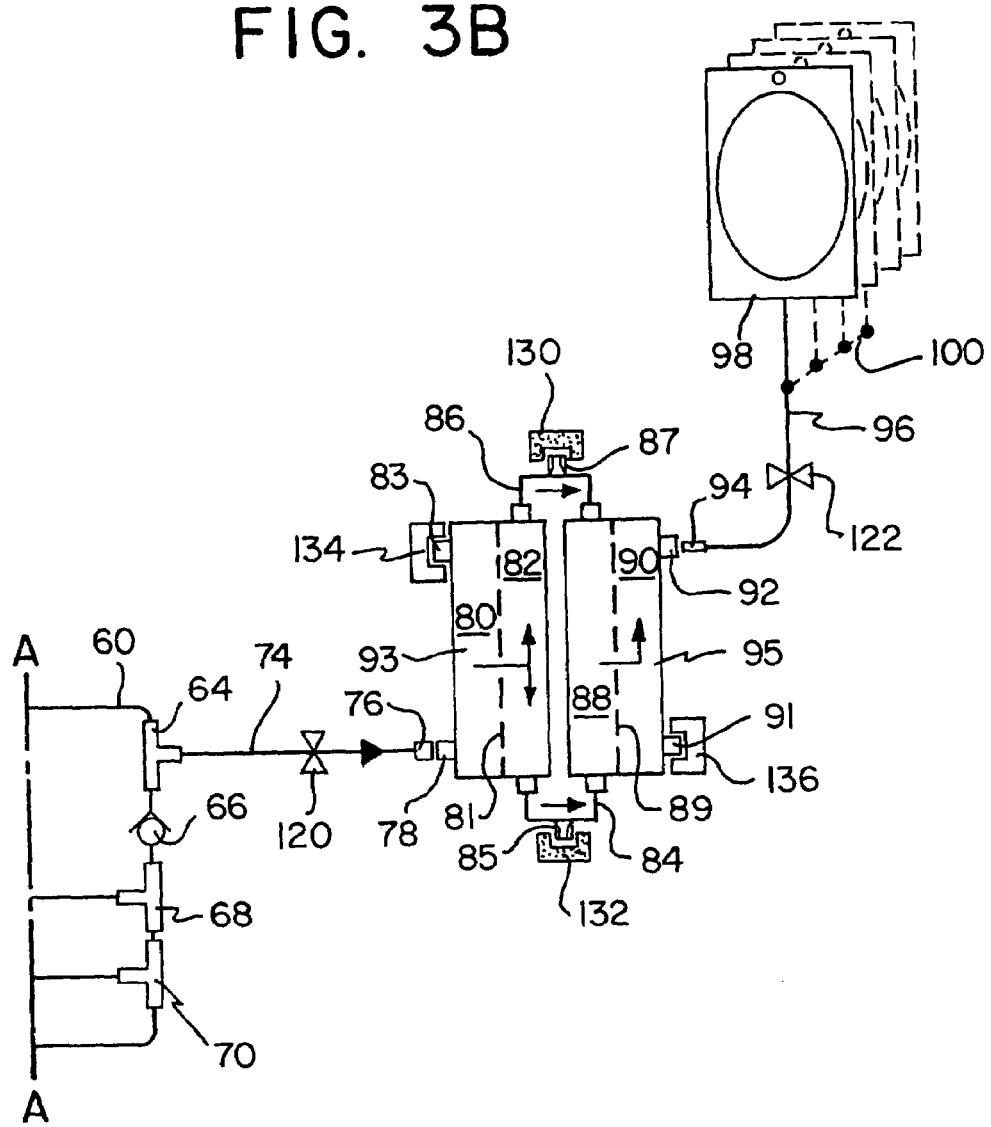

An alternative to the embodiment of FIGS. 2A and 2B is shown schematically in FIGS. 3A and 3B. Here the fluid contained in the reservoir 162 is made up of the dialysate fluid exiting the machine through conduit 46. The fluid reservoir 160 includes a weir 163 such that excess dialysate fluid overflows into a separate compartment that leads out to the drain. This has the advantage of always having a full reservoir of fluid used in the process of making sterile fluid. A second advantage is that this configuration provides an efficient use of fluid being used in the process.

Other than the differences in fluid flow path resulting from the above structual differences, the method of generating a sterile fluid in accordance with the configuration of FIGS. 3A and 3B is carried out substantially as described above with reference to the embodiment of FIGS. 2A and 2B.

Figure 4A:
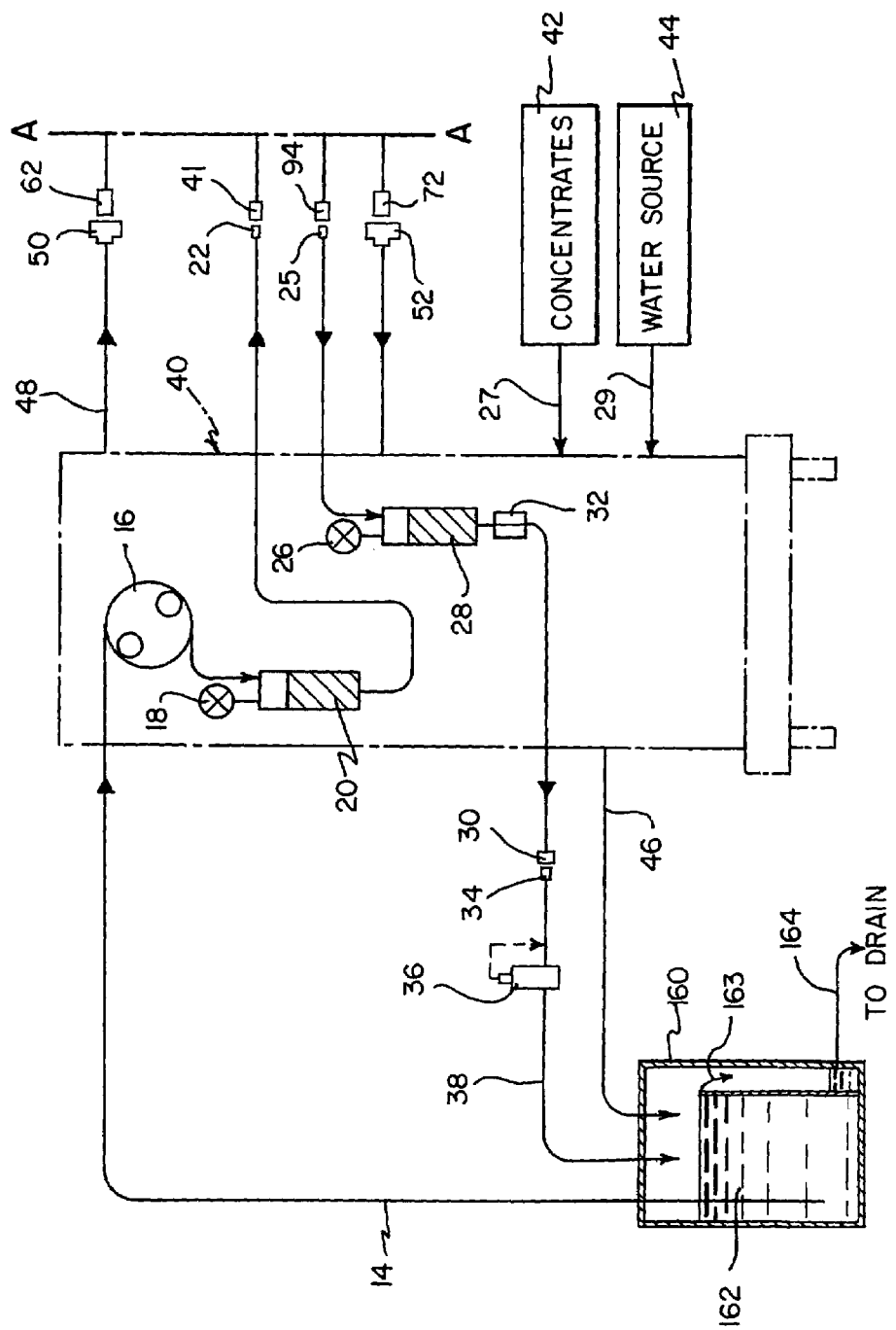
FIGS. 4A and 4B, when joined at the match line A—A, are a schematic illustration of a fluid sterilization system in accordance with a fourth embodiment in which a control unit is added to the fluid sterilization system of FIGS. 3A and 3B.
Figure 4B:
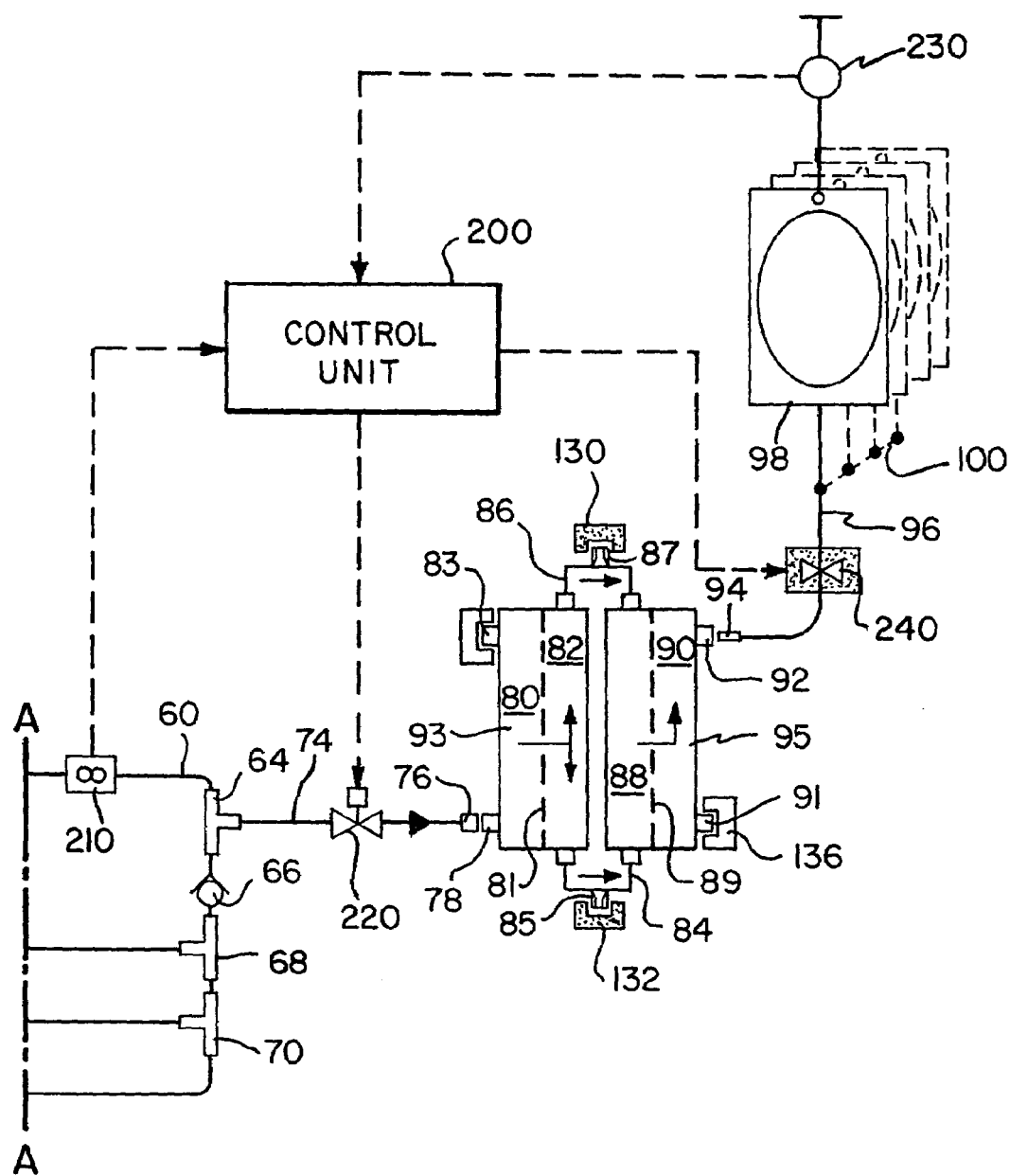

Another embodiment of the invention is illustrated in FIGS. 4A and 4B. The configuration of this embodiment may be identical (both structurally and functionally) to that of the above embodiments except that a control unit 200 may be used to automate part of the process. For example, a load cell 230 may be used as input device to the control unit as a means to regulate how much sterile fluid is placed into one or several of the collection bags 98 or 110, respectively. Operation may be such that when the load cell 230 senses the collection bag is full or at a desired set point, the control unit may close a pinch valve 240 that is positioned on the bag inlet tubing conduit 96. When the pinch valve is closed, the user can load empty bags and restart the filling process.

Another embodiment of FIGS. 4A and 4B is an added safety mechanism that would aid in preventing fluid circulating back and forth from reservoir 160 from entering the conduit 74 leading to the sterilizing filters 93, 95. This may be accomplished by using a flow sensor device 210 in the dialysate conduit 60. The flow sensor device 210 may be any one of those known in the art, such as flow switch, a turbine style flow meter, an ultrasonic flow meter, or a flow meter based on a heated thermistor or thermal dilution methods. Operation is such that when dialysate flow is stopped, such as when the machine goes into a bypass state, the flow sensor 210 detects the change. This signal is then used as an input to the control unit 200, which closes a solenoid actuated valve 220 to stop the flow of fluid toward the sterilizing filters. In this manner, even if the check valve 66 were to fail, fluid downstream of the check valve would not be able to back up into the sterilizing filters. After dialysate flow from the machine has been re-initiated, the flow sensor 210 can send a signal to the control unit 200 to re-open valve 220 and thus resume making sterile fluid.

Figure 5A:
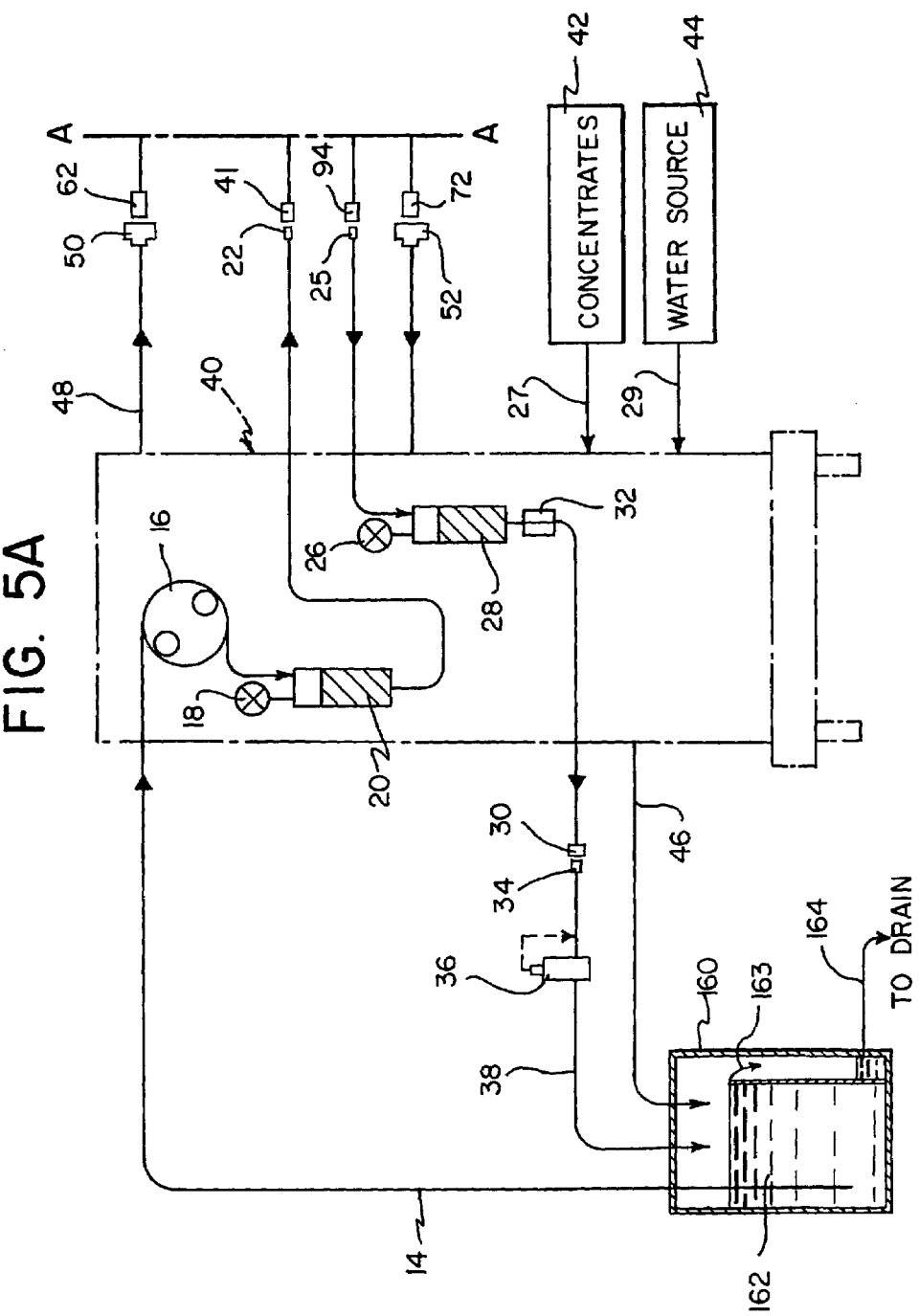
FIGS. 5A and 5B, when joined at the match line A—A, are a schematic illustration of a fluid sterilization system in accordance with a fifth embodiment, wherein a hydrophobic sterile filter and a rinse fluid collection container are used as aids to prime and rinse a sterilizing filter.
Figure 5B:
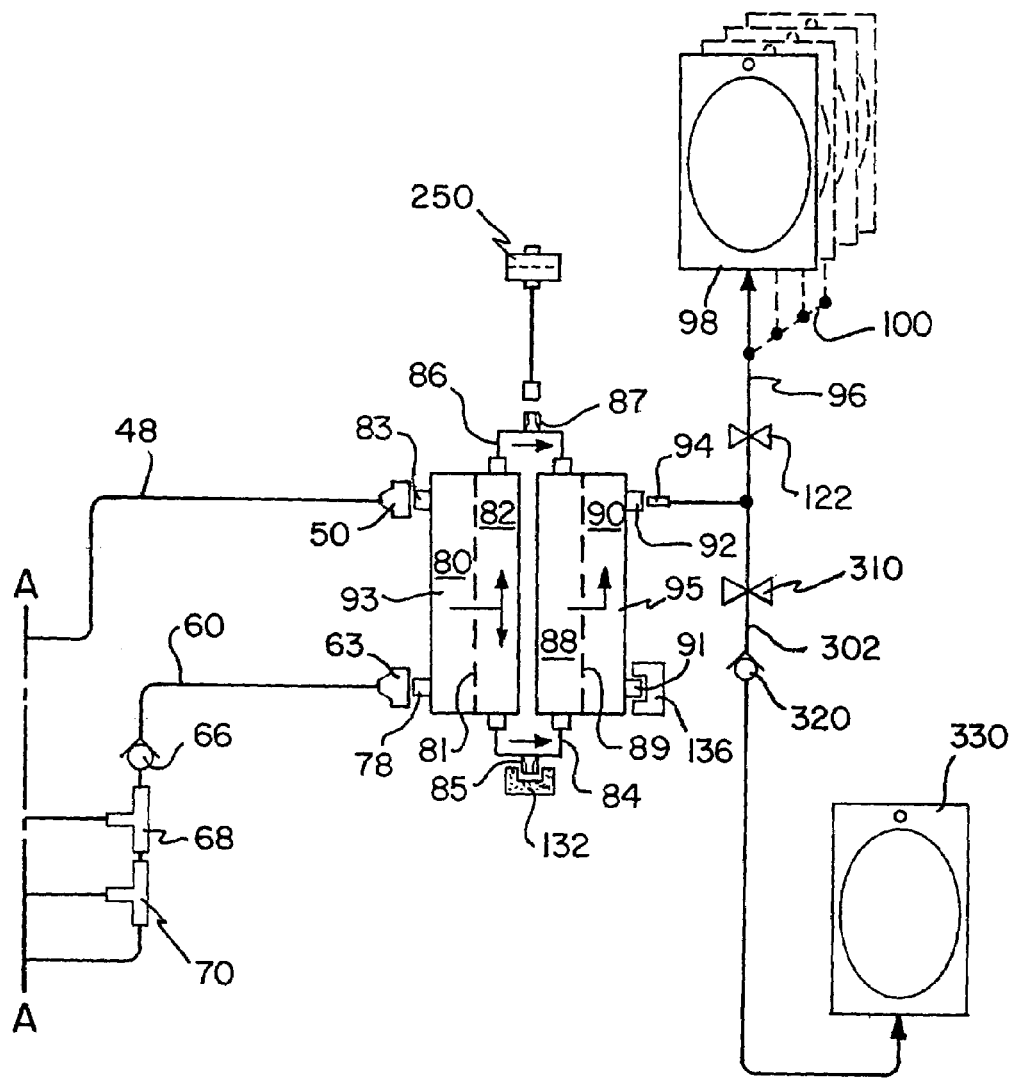

FIGS. 5A and 5B schematically illustrate an alternative configuration of the embodiment of FIGS. 3A and 3B. In the configuration of FIGS. SA and 5B, connection of the dialysate supply connector 50 is made directly to an inlet port 83 of the upstream compartment 80 of the first sterilizing filter 93. Connector 63, which is at the inlet end of conduit 60, is connected to an outlet port 78 of the upstream compartment 80 of the first sterilizing filter 93. Dialysate fluid (not sterile) that is not filtered across the first semi-permeable membrane 81, flows within the upstream compartment 80 to outlet port 78. The dialysate fluid then flows within conduit 60 and conduit 54 as it returns to the machine 40. This embodiment operates in substantially the same manner as the embodiment shown in FIGS. 4A and 4B in that as the fluid pressure increases in the fluid path, more and more non-sterile dialysate fluid is conducted across the semi-permeable membrane 81 as a result of the increase in system pressure.

In addition, a sterile hydrophobic filter can be placed at an upper end of the sterilizing filters that is in fluid communication with the downstream compartment 82 of the first sterilizing filter 93 and the upstream compartment 88 of the second sterilizing filter 95. In the outlet conduit 300 of the second sterilizing filter 95, a tee junction is used to divert the flow to either an initial rinse collection bag 330 or the sterile collection bag 98. The advantages of this configuration is to aid in priming the sterilizing filters and performing an initial rinse of the sterilizing filters that may be necessary to flush out residual chemicals as a result of the filtering manufacturing process. This will become more evident as the priming method is described. Generally, filters are shipped in a dry or empty state and thus must be primed and rinsed prior to use. Upon connecting up dry sterilizing filters as shown in FIGS. 5A and 5B, the upstream compartment 80 of the first sterilizing filter 93 is purged of air when dialysate flow through conduit 48 is initiated in a similar manner as priming a new dialyzer before treatment. Once the air has been purged out of compartment 80, fluid will filter across the first semi-permeable membrane 81 and flow into the downstream compartment 82. Because the downstream compartment 82 and the upstream compartment 88 are in fluid communication, both compartments will fill from the bottom end and thus purging air out of a hydrophobic filter 250. After most of the air has been purged out through the hydrophobic filter 250, the fluid will come into contact with the hydrophobic filter 250.

Because the filter 250 is of a hydrophobic type, the fluid will not be able to pass though the hydrophobic membrane of the filter 250 as is known in the art. The fluid in the upstream compartment 88 of the second sterilizing filter 95 will then filter across the semi-permeable membrane 89 and flow into the downstream compartment 90. Here the twice filter fluid flows through conduit 300 that leads to a tee. Initially, clamp 312 is kept in a closed position and clamp 310 is open to direct the outlet air and fluid to the initial rinse collection bag 330. Given the rinse collection bag 330 is a fixed volume, this permits a predetermined amount of fluid to be rinse through the sterilizing filters prior to collecting fluid in the sterile collection bags 98, 110. This volume can be specific to ensure any residual components in the sterilizing filter are substantially removed. A check valve 320 or the like may be placed in the conduit 302 leading to the rinse collection bag to prevent flow of fluid from this bag to the sterile collection bags 98, 110. It is preferred to keep the rinse collection bag suspended below the sterile collection bags such that it remains at a lower hydrostatic pressure than the other bags. After the rinse bag is full, clamp 310 can be closed and clamp 312 can be opened to begin collecting the sterile fluid in the same manner as described in the previous embodiments.

Figure 6B:
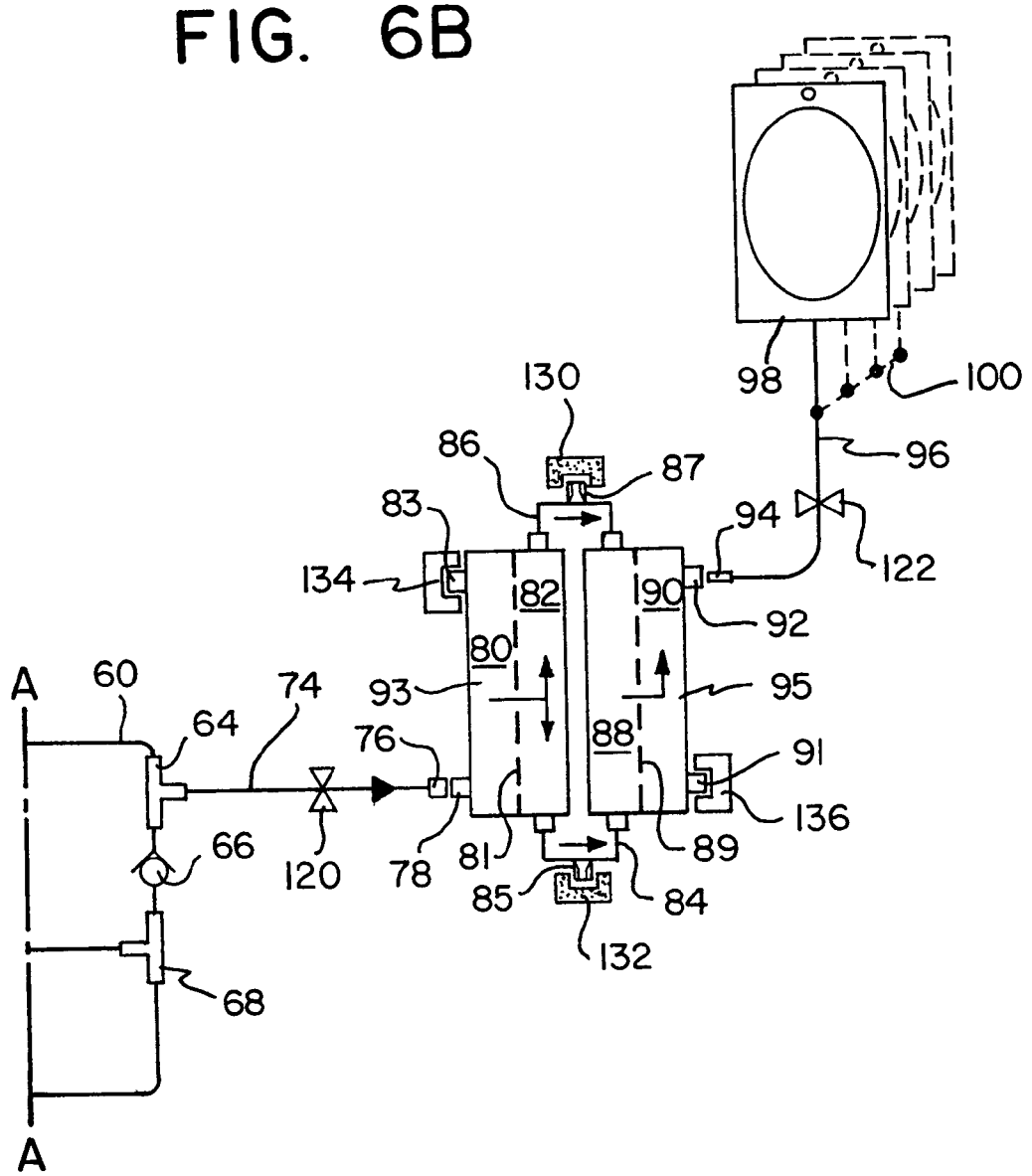

Now referring to FIGS. 6A and 6B which illustrate yet another embodiment. The embodiment of FIGS. 6A and 6B is similar to the embodiment of FIGS. 3A and 3B and therefore, like elements have been numbered alike. The conduit 14 includes a portion 402 that acts as a pump inlet line for drawing the fluid contained in the fluid reservoir 160 and a pump outlet line 404 that delivers the pumped fluid under pressure to the connector 68 (which is at a location downstream of the check valve 66). In this embodiment, a pump recirculating line 400 is provided and includes a first end and a second end with the first end being fluidly connected to the pump inlet line 402 and the second end is fluidly connected to the pump outlet line 404. The pump recirculating line 400 contains the back pressure regulating valve 36 which operates in the same manner as in the embodiment of FIGS. 3A and 3B.

The back pressure regulating valve 36 functions so that the fluid being returned through the pump recirculating line 400 constitutes higher pressure fluid that is being pumped by pump 16 as opposed to fluid contained in the conduit 60 (as in FIGS. 3A and 3B). In addition, another advantage of this embodiment is that the fluid being returned does not have to be returned back the fluid reservoir 160 but rather only has to be returned to the fluid inlet side of the pump 16, e.g., to the pump inlet line 402. Conventional connectors, such as T-connectors, can be used to provide fluid connections between the conduits. The other components of this embodiment function in the same manner and thus the observed pressure increase in the fluid path results in non-sterile dialysate fluid flowing to the sterilizing filters 93, 95 for sterilization thereof.

The present application provides several apparatuses and methods for conveniently and effectively producing a sterilization fluid in an "on-site" manner using a machine, such as a dialysis machine. Advantageously, the present sterilization system is designed to be fitted with conventional equipment that produces non-sterile fluid. Particular utility is found when the sterilization system is used with a dialysis machine as a means for producing sterile infusion fluid.

It will be appreciated by persons skilled in the art to which this invention pertains that the invention is not limited to the preferred embodiments and configurations described above and with reference to the accompanying drawings. Rather, the scope of the invention is limited only by the following claims.

What is claimed is:

1. A system for generating a sterile infusion fluid comprising: a machine for producing non-sterile infusion fluid, the machine having an outflow line for discharging the non-sterile infusion fluid from the machine and a return line for receiving a fluid, the outflow line including an outlet connector and the return line including a return connector; a first conduit having first and second ends with a first connector at the first end for mating with the outlet connector and a second connector at the second end for mating with the return connector, the first conduit having a third connector permitting at least a portion of the non-sterile infusion fluid to be diverted from the first conduit under select conditions, the first conduit further including a first valve disposed between the third connector and the second connector; a second conduit connected at one end to the third connector, the second conduit being connected at an opposite end to a filtration assembly including at least one sterilization filter for sterilizing the diverted non-sterile infusion fluid; and a device for increasing fluid pressure within the first conduit at a location downstream of the first valve so as to cause a fluid pressure increase in the return and outflow lines resulting in at least a portion of the non-sterile infusion fluid being diverted from the first conduit and into the second conduit wherein the first valve comprises a check valve configured to permit fluid flow in a direction from the first end of the first conduit toward the second end of the first conduit.

2. The system of claim 1, wherein the machine is a dialysis machine and the non-sterile infusion fluid is a non-sterile dialysate fluid.

3. The system of claim 1, wherein the fluid received in the return line includes the non-sterile infusion fluid.

4. The system of claim 1, wherein the device for increasing fluid pressure includes a source of second fluid and a third conduit which is fluidly connected at one end to the source and is connected at an opposite end to the first conduit at the location downstream of the first valve, the device injecting the second fluid under pressure into the first conduit at the downstream location.

5. The system of claim 4, further including a fourth connector at the downstream location, the fourth connector receiving the pressurized second fluid which is injected into the non-sterile infusion fluid flowing through the first conduit.

6. The system of claim 4, wherein the second fluid is water.

7. The system of claim 4, wherein the second fluid is water and the second fluid source is the same fluid source that supplies water to a proportioning system or the machine, the proportioning system mixing the water with infusion concentrate at a predetermined proportion to produce non-sterile infusion fluid of a predetermined concentration.

8. The system of claim 4, further including a pressure regulator disposed within the third conduit for regulating the downstream fluid pressure of the second fluid flowing within the third conduit, thereby also regulating the rate of injection of the second fluid into the first conduit and the pressure increase observed in the first conduit.

9. The system of claim 8, wherein the fluid pressure within the third conduit is from about 2 psi to about 10 psi.

10. The system of claim 4, wherein the second fluid is of a type that is both miscible with the non-sterile infusion fluid and compatible with any materials that are present in any flow path communicating with the machine, including the return line.

11. The system of claim 1, wherein the filtration assembly includes two sterilization filters connected in series to provide redundant sterilization of the infusion fluid.

12. The system of claim 1, further including a device for storing the sterilized infusion fluid.

13. The system of claim 12, wherein the storage device comprises at least one sterile collection bag which is in fluid communication with an outlet port of the at least one sterilization filter.

14. The system of claim 1, further including a fluid reservoir containing a second fluid and wherein the device for increasing fluid pressure includes a reservoir outflow conduit in fluid communication with the fluid reservoir at one end, the reservoir outflow conduit being connected at an opposite end thereof to the first conduit at the location downstream of the first valve, a pump being provided for drawing the second fluid from the fluid reservoir and through the reservoir outflow conduit and into the first conduit under pressure, the device further including a reservoir inflow conduit for receiving fluid flowing within the first conduit, the reservoir inflow conduit being fluidly connected to the first conduit, a back pressure regulator being provided in the reservoir inflow conduit for generating a back pressure, thereby causing the fluid pressure increase in the first conduit, the return line, and the outflow line.

15. The system of claim 1, wherein the device for increasing fluid pressure includes a fluid reservoir holding a second fluid, a pump for withdrawing the second fluid from the fluid reservoir through a pump inlet line and delivering the second fluid under pressure through a pump outlet line to the downstream location of the first valve, and a back pressure regulator being provided in a pump recirculating line that is in fluid communication with the fluid in the pump inlet line and the pump outlet line, thereby causing the fluid pressure increase in the first conduit, the return line, and the outflow line.

16. The system of claim 14, further including a drain conduit for discharging unwanted fluid from the machine, the drain conduit being in fluid communication with the fluid reservoir such that the second fluid comprises the unwanted fluid that has been discharged from the machine.

17. The system of claim 1, further including a control unit, the control unit including a flow sensor device located in the first conduit for monitoring the flow properties of the non-sterile infusion fluid.

18. The system of claim 17, further including a second valve disposed in the second conduit and being in communication with the control unit, the control unit signaling the second valve to close when the sensor detects that the non-sterile infusion fluid is no longer flowing through the first conduit the second valve being reopened once the sensor detects flow of the non-sterile infusion fluid through the first conduit.

19. The system of claim 17 further including a device for storing the sterilized infusion fluid, the control unit including a sensor associated with the storage device for detecting when a predetermined amount of the sterilized infusion fluid is present in the storage device, the control unit being in communication with a third valve disposed in a conduit connecting the filtration assembly to the storage device, the control unit signaling the third valve to close once the predetermined amount is achieved.

20. The system of claim 1, wherein the machine includes a flow balancing mechanism for regulating flow rate of the non-sterile fluid being produced by the machine and regulating the flow rate of the fluid being returned to the machine through the return line.

21. A system of claim 13, further including a rinse collection bag that is filled prior to the filing of the sterile collection bag, the rinse collection bag being in fluid communication through a collection conduit with an outlet port of the at least one sterilizing filter, a valve being disposed within the collection conduit so that once the rinse collection bag is filled to a predetermined level, the sterile infusion fluid is diverted to the sterile collection bag.

22. A method of generating a sterile infusion fluid, the method comprising:
producing non-sterile infusion fluid with a machine having an outflow line for discharging the non-sterile infusion fluid from the machine and a return line for receiving a fluid;
connecting a first conduit between the outflow line and the return line, the first conduit having a first connector permitting at least a portion of the non-sterile infusion fluid to be diverted from the first conduit under select conditions, the first conduit including a valve located downstream of the first connector, the valve permitting fluid within the first conduit to flow only in a direction from the outflow line towards the return line;
connecting a second conduit at one end to the first connector, the second conduit being connected at an opposite end to a filtration assembly including at least one sterilization filter for sterilizing the diverted non-sterile infusion fluid;
discharging the non-sterile infusion fluid through the outflow line; and increasing the fluid pressure within the first conduit at a location downstream of the valve so as to cause a fluid pressure increase in each of the first conduit, the return line, and the outflow line resulting in the at least a portion of the non-sterile infusion fluid being diverted from the first conduit and into the second conduit through which the non-sterile infusion fluid flows to the filtration assembly.

23. The method of claim 22, wherein increasing the fluid pressure comprises:

injecting a second fluid under pressure through a third conduit into the first conduit at the location downstream of the valve so as to cause the fluid pressure increase.

24. The method of claim 23, wherein the degree of pressure of which the second fluid is injected into the first conduit is adjusted by a pressure regulator in the third conduit.

25. The method of claim 23, wherein the second fluid is from the same fluid source that is supplied to the machine for preparing the non-sterile infusion fluid.

26. The method of claim 23, wherein injecting the second fluid comprises:

pumping the second fluid through a third conduit from a fluid reservoir and into the first conduit at the location downstream of the valve and increasing the fluid pressure further includes setting a back pressure regulator to generate a back pressure in a fourth conduit that is in fluid communication with the first conduit.

27. The method of claim 26, wherein the second fluid comprises waste fluid that is discharged from the machine to the fluid reservoir, a drain run-off outlet being provided with the fluid reservoir for discharging excess second fluid from the fluid reservoir.

* * * * *